United States Patent [19]

Floyd, Jr. et al.

[11] Patent Number: 4,730,065

[45] Date of Patent: Mar. 8, 1988

[54] 15-DEOXY-16-HYDROXY-16-SUBSTITUTED PROSTANOIC ACIDS AND CONGENERS

[75] Inventors: Middleton B. Floyd, Jr., Suffern, N.Y.; Martin J. Weiss, Fort Lee, N.J.; Charles V. Grudzinskas, Upper Nyack, N.Y.; Sow-Mei L. Chen, Park Ridge, N.J.

[73] Assignee: American Cyanamid Company, Stamford, Conn.

[21] Appl. No.: 77,042

[22] Filed: Jul. 24, 1987

Related U.S. Application Data

[60] Continuation of Ser. No. 931,896, Nov. 17, 1986, abandoned, which is a continuation of Ser. No. 680,208, Dec. 10, 1984, abandoned, which is a division of Ser. No. 337,425, Jan. 6, 1982, Pat. No. 4,504,417, which is a division of Ser. No. 305,901, Sep. 25, 1981, Pat. No. 4,429,148, which is a division of Ser. No. 79,126, Sep. 26, 1979, Pat. No. 4,328,358, which is a division of Ser. No. 835,614, Sep. 22, 1977, Pat. No. 4,192,950, which is a division of Ser. No. 706,343, Jul. 19, 1986, Pat. No. 4,061,670.

[51] Int. Cl.$^4$ .............................................. C07C 177/00
[52] U.S. Cl. ....................................... 556/21; 556/87; 556/465; 568/849
[58] Field of Search ......................... 556/21, 87, 465; 568/844

[56] References Cited

U.S. PATENT DOCUMENTS

| | | | |
|---|---|---|---|
| 3,950,406 | 4/1976 | Floyd | 562/503 |
| 3,965,143 | 6/1976 | Collins | 560/121 |
| 4,028,396 | 6/1977 | Schaub | 560/121 |
| 4,113,967 | 9/1978 | Weiss | 560/121 |

Primary Examiner—Robert Gerstl
Attorney, Agent, or Firm—Robert P. Raymond

[57] ABSTRACT

This disclosure describes novel 15-deoxy-16-hydroxy-16-substituted prostanoic acids and congeners thereof having utility as bronchodilators as hypotensive agents, and as agents for the control of excessive gastric secretion.

14 Claims, No Drawings

15-DEOXY-16-HYDROXY-16-SUBSTITUTED PROSTANOIC ACIDS AND CONGENERS

This application is a continuation of application Ser. No. 931,896, filed 11/17/86, abandoned which is a continuation of application Ser. No. 680,208 filed 12/10/84, abandoned which is a division of copending application Ser. No. 337,425, filed Jan. 6, 1982, which is a division of application Ser. No. 305,901, filed Sept. 25, 1981, now U.S. Pat. No. 4,429,148, which is a division of application Ser. No. 79,126, filed Sept. 26, 1979, now U.S. Pat. No. 4,328,358, which is a division of application Ser. No. 835,614, filed Sept. 22, 1977, now U.S. Pat. No. 4,192,950, which is a division of application Ser. No. 706,343, filed July 19, 1976, now U.S. Pat. No. 4,061,670.

BRIEF SUMMARY OF THE INVENTION

This invention relates to novel 15-deoxy-16-hydroxy-16-substituted prostanoic acids and cogeners thereof, as well as to intermediates and methods for their preparation.

The novel compounds of this invention embrace all the optical antipodes, racemic mixtures and diasteromeric mixtures corresponding to the following general formula, the absolute configuration of which is that of the natural mammalian prostaglandins.

The compounds of this invention may be represented by the following general formula and the mirror image thereof;

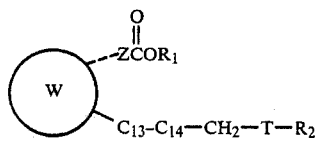

wherein W is selected from the group comprising

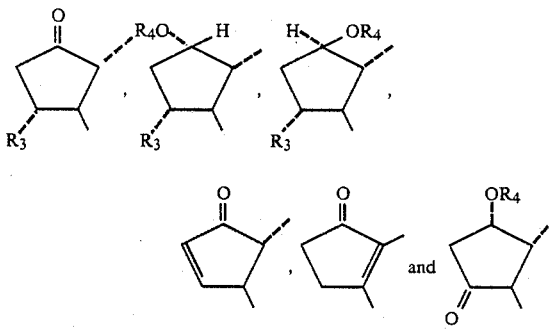

wherein $R_1$ is selected from the group comprising hydrogen and lower alkyl ($C_1$–$C_{12}$); $R_2$ is an alkyl or alkenylmethyl group ($C_3$–$C_7$) optionally substituted with one or two alkyl groups of one to three carbon atoms; $R_3$ is selected from the group comprising hydrogen, hydroxyl, alkanoyloxy ($C_2$–$C_6$), triloweralkylsilyloxy, tetrahydropyran-2-yloxy and alkoxy ($C_1$–$C_3$); $R_4$ is selected from the group comprising hydrogen and alkanoyloxy ($C_2$–$C_6$); T is the divalent radical

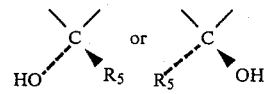

wherein $R_5$ is selected from the group comprising vinyl, methylvinyl and cyclopropyl; the moiety $C_{13}$–$C_{14}$ is either trans-vinylene or ethylene; and Z is selected from the group comprising —$(CH_2)_6$, —$CH_2$—CH=CH—$(CH_2)_n$, $(CH_2)_n$—S—$CH_2$ and $(CH_2)_n$—O—$CH_2$, with the proviso that when Z is $(CH_2)_nSCH_2$, then $R_3$ must not be an oxy function, with the further proviso that when Z is $(CH_2)_nSCH_2$, then the cyclopentanone ring may not contain a double bond; where n is an integer from 3 to 5; and when $R_1$ is hydrogen, the pharmaceutically acceptable salts thereof.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g. lithium, sodium and potassium, and from the alkaline earth metals, e.g. magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atoms, as well as heterocyclic amines, e.g. piperidine, morpholine, pyrrolidine, piperazine and lower alkyl derivative thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

DETAILED DESCRIPTION OF THE INVENTION

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic solutions are preferred. For that purpose, it is preferred, because of increased water solubility, that $R_1$ be hydrogen or a pharmacologically acceptable cation. For subcutaneous or intramuscular injection sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom, et al., *J. Biol. Chem.*, 238, 3555 (1963) and Horten, *Experientia,* 21, 113 (1965) and references cited therein. All of the so called natural prostaglandins are derivatives of prostanoic acid:

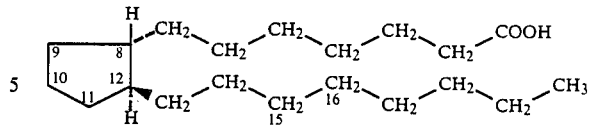

The hydrogen atoms attached to C-8 and C-12 are in transconfiguration. The natural prostaglandins represent only one of the possible optical isomers. The compounds of this invention include all possible optical isomers and racemates.

The configuration of substituents on the prostaglandin molecule are designed to be in the α-configuration if they lie beneath the plane of the molecule as drawn above and are designated with a - - - - bond. Those substitutents which lie above the plane of the molecule as drawn above are designated β and are represented by a ▬bond.

The novel compounds of this invention can be prepared by a novel 1,4-conjugate-addition procedure involving treatment of the ether blocked cyclopentenone (15) with a lithio-cuprate reagent such as (13) prepared as illustrated in Flowsheet A, in which $R_2$, $R_3$, $R_4$, $R_5$, W and n are as hereinabove described. $R_1'$ is lower alkyl ($C_1$–$C_{12}$) or, trilower alkylsilyl, or tetrahydropyran-2-yl and $R_3'$ is hydrogen, triloweralkylsilyloxy or tetrahydropyran-2-yloxy.

FLOWSHEET A

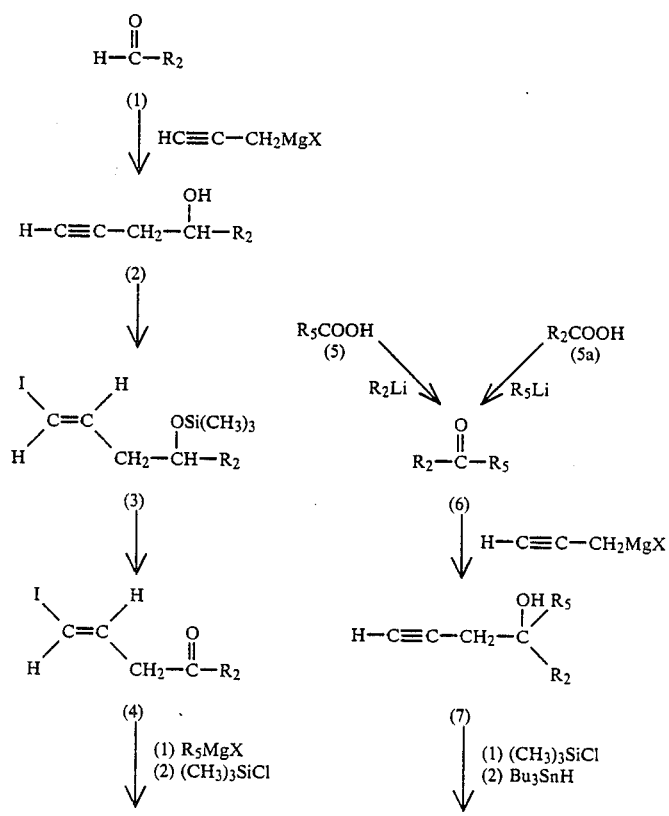

-continued
FLOWSHEET A
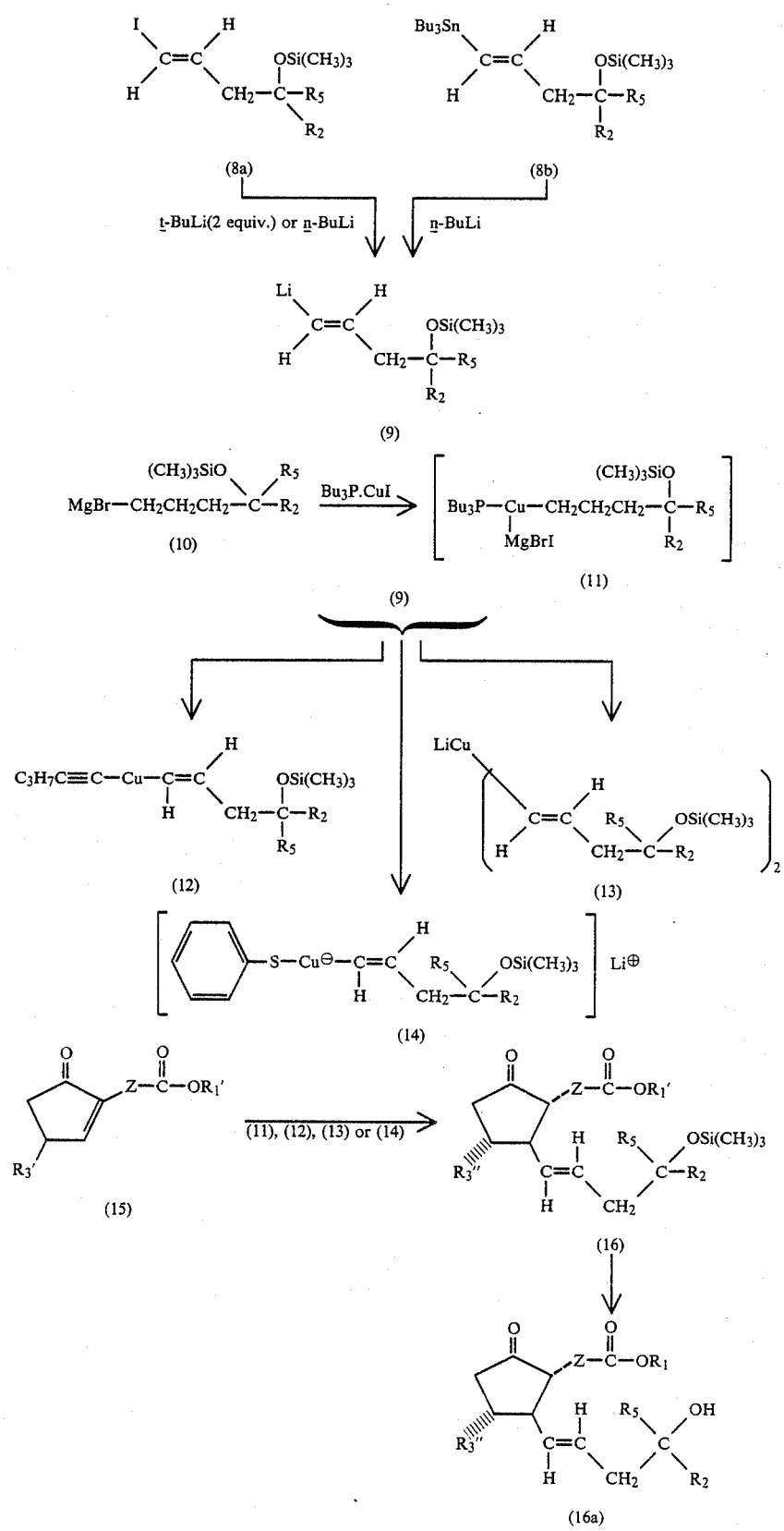
In accordance with the procedure as outlined in Flowsheet A, an aldehyde (1) is treated with propar- The trimethylsilyl protecting group is removed with mild acid and the resulting vinyl iodide alcohol is oxidized with pyridinium chlorochromate to provide the 1-iodo-4-oxo-trans-1-alkene (4), which upon treatment with a Grignard reagent ($R_5MgX$) provides the 1-iodo-4-hydroxy-trans-1-alkene, which is silylated in the usual manner to provide the silyl ether (8a).

A more preferred method for the preparation of the vinyllithium intermediate (9) is also described in Flowsheet A. Treatment of the requisite carboxylic acid (5 or 5a) with the appropriate organolithium reagent ($R_2Li$ or $R_5Li$ respectively) gives the corresponding ketone (6) which upon treatment with propargylic magnesium halide provides the homopropargylic alcohol (7) which is converted to the trans vinylstannyl derivative by sequential treatment with chlorotrimethylsilane and tri-n-butylstanyl hydride in the presence of azobisisobutrylnitrile. Treatment of the vinylstannyl reagent (8b) with n-butyllithium at a temperature of $-10°$ to $-78°$ C. generates the vinyllithium reagent (9).

Treatment of (8a) at low temperature, preferably $-30°$ C. to $-78°$ C. in an inert solvent, e.g. hexane, ether or toluene, with an alkyl lithium, e.g. n-butyl lithium or t-butyl lithium (2 equivalents) provides the trans-1-alkenyl lithium reagent (9). In the case of the vinylstannyl (8b) n-butyllithium is preferred for the generation of the vinyl lithium reagent.

For the preparation of the asymmetrical lithio cuprate (12) or the like, a solution of one molar equivalent of copper (I)-1-alkyne, preferably copper (I)-1-pentyne in anhydrous tributylphosphine or HMPTA, preferably one to five molar equivalents in ether is added to one molar equivalent of the aforementioned vinyl-lithium solution cooled to about $-78°$ C. After about one hour at this temperature, a molar equivalent of the requisite cyclopentenone (15) is added. After several hours at $-30°$ C. to $-70°$ C. the reaction mixture is quenched with aqueous ammonium chloride solution and the blocked product (16) is isolated in the usual manner.

It is also possible to effect conjugate 1,4-addition with the asymmetrical lithio cuprate (14) derived from vinyl lithium (9) and cuprous thiophenoxide. A solution of vinyl lithium (9) in ether at $-78°$ C. is reacted with an equimolar amount of a reagent prepared by admixture, in ether at a temperature of $0°$ C. to $-78°$ C., of equimolar amounts of cuprous thiophenoxide and copper (I) iodide tributylphosphonium complex. After about 30 minutes at this temperature, the lithio cuprate (14) is treated with the requisite cyclopentenone (15) as described hereinabove for the conjugate addition with 1-alkynyl lithio cuprate (12).

For the preparation of the symmetrical lithio cuprate (13) one molar equivalent of copper (I) iodide tributylphosphine complex, dissolved in anhydrous ether, is added at about $-78°$ C. to two molar equivalents of the aforementioned vinyl iodide (9) solution in hexanes, cooled to $-78°$ C. After about one hour at this temperature, the lithio cuprate (13) is treated with the requisite cyclopentenone (15) as described hereinabove for the conjugate addition with the 1-alkynyl lithio cuprate (12).

The procedures for conjugate addition involving organocopper reagents are well known in the art, see for example C. J. Sih, et al., *J. Amer. Chem. Soc.*, 97, 865 (1975).

In the cases were $R_1'$=trimethylsilyloxy in cyclopentenone (15) the conjugate addition is performed at $-78°$ C. to $-40°$ C. The reaction is quenched by addition of an ether solution of acetic acid. Removal of blocking groups is then carried out as described in the reference above to provide the product (16a) wherein $R_1$, $R_2$ are as hereinabove defined and $R_3''$ is hydrogen or hydroxyl.

All available evidence leads us to believe that the

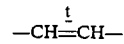

function introduced by the cuprate process occupies a position trans to the 11-oxy function. Similarly, we are led to the conclusion that in the product (16) the two side-chains attached to $C_8$ and $C_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ε. In order to ensure a trans-relationship in (16) these products can be submitted to conditions known in the literature to equilibrate the cis-8-iso-$PEG_1$ to a mixture containing about 90% of the trans product. These conditions involve treatment with potassium acetate in aqueous methanol for 96 hours at room temperature.

The triloweralkylsilyloxy substituted lithio-cuprate reagents of type (12) and its iodo and trialkylstannyl precursors are novel and useful compounds which are also embraced by this invention. They may be defined by generic formulae (A) and (B).

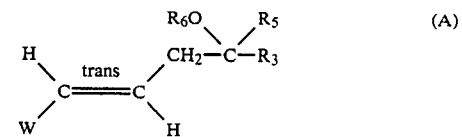

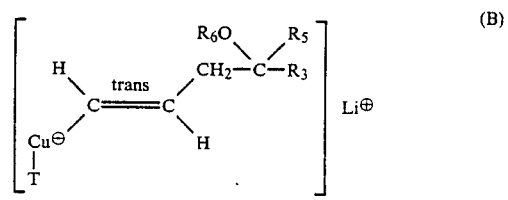

wherein W is iodine or tri n-butylstannyl, $R_3$ and $R_5$ are as hereinabove defined, $R_6$ is hydrogen or triloweralkylsilyl, T is thiopheneoxide, substituted thiopheneoxide, an alkyne or the identical vinyl moiety.

The 13-dihydro derivatives can be prepared, as shown in Flowsheet A, by treating cycloalkenones of formula (15) with Grignard reagent such as (10), in the usual manner in the presence of a catalyst such as the tributylphosphine-cuprous-iodide complex. The trimethylsilyl and other blocking groups are then removed in the usual manner as described hereinabove.

In accordance with Flowsheet B, when the 11-hydroxy derivatives ($R_1$=hydroxy) or the 11-oxy derivatives embraced by (17) are treated with dilute acid, or dilute base, it is possible to effect elimination and the formation of the corresponding $\Delta^{10}$ derivatives (18) prostaglandins of the A type. A preferred procedure involves treatment in tetrahydrofuran:water (2:1) solvent with 0.5N in HCl for about 70 hours at ambient temperatures or alternatively in methanol-water solvent (1:5) with 0.2M potassium carbonate for 16 hours at ambient temperatures. Under acidic conditions, a tetrahydropyranyl or trialkylsilyl ester will undergo hydrolysis.

FLOWSHEET B

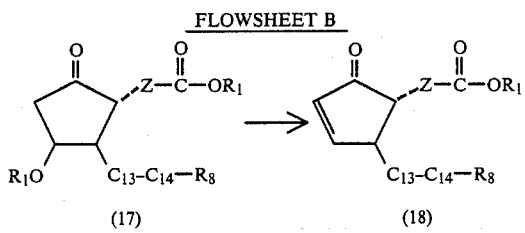

(17)        (18)

In Flowsheet B, $R_1$, Z and $C_{13}$-$C_{14}$ are as hereinabove defined and $R_8$ is the moiety

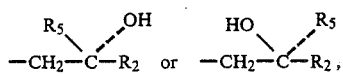

wherein $R_2$ and $R_5$ are as hereinabove described.

The 11-oxy-9-keto derivatives of this invention can be converted to the corresponding 9-hydroxy derivatives as described in Flowsheet C. If this conversion is effected with sodium borohydride, the product is a mixture of 9α- and 9β-hydroxy derivatives (19) and (20) respectively, as set forth in the following reaction scheme, wherein $R_1$, $R_3$, Z and $C_{13}$-$C_{14}$ are as hereinabove defined, and $R_8$ is the moiety

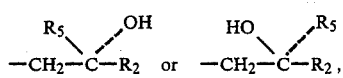

wherein $R_2$ and $R_5$ are as hereinabove defined.

FLOWSHEET C

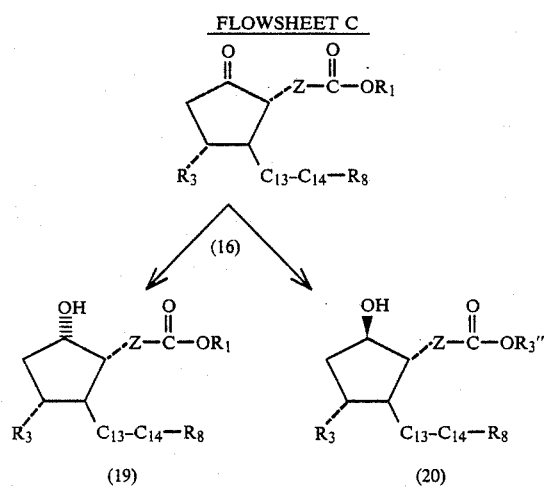

(19)        (20)

When the reaction is carried out with lithium perhydro-9b-boraphenylyl hydride [H. C. Brown and W. C. Dickason, J.A.C.S., 92, 709, (1970)] or lithium tris-(t-butyl)-borohydride [H. C. Brown and S. Krishnamurthy, ibid., 94, 7159 (1972)] the product is at least predominantly the 9α-hydroxy derivative wherein the 9-hydroxy group is cis to the side chain attached to $C_8$ and to the 11-oxy function, if present. In accordance with accepted convention, and α-substituent at the 8-, 9-, 11- or 12-positions is behind the plane of the paper, whereas a β-substituent at these positions is in front of the plane of paper. This is usually represented by a - - - bond for an α-substituent, a ▬ bond for a β-substituent, and a ∼ bond where both are indicated.

In accordance with Flowsheet D, wherein $R_9$ is hydrogen or lower alkyl ($C_1$-$C_9$) and Z, $R_8$ and $C_{13}$-$C_{14}$ are as described hereinabove, treatment of PGFα analogs with an oxidizing agent such as Jones reagent or pyridinium chlorochromate provides a selective oxidation of the 11α-hydroxyl to provide compounds of the PGD structure such as (22).

FLOWSHEET D

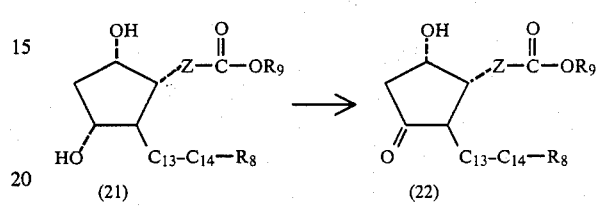

(21)        (22)

The carboxylic acids of this invention can be readily converted to the various alkyl esters of this invention by treatment in the usual manner with the appropriate diazoalkane. The preparation of diazoalkanes by various procedures are well described in the art. See for example C. D. Gutsche, Organic Reactions, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides is then treated with the appropriate alcohol to give the derivatized product. [For a pertinent literature analogy see Prostaglandins, 4, 738 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see German Offen. 2,365,205; Chem. Abst., 81, 120098g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19-27 (August 1973) as well as references cited therein. Additional information concerning high speed liquid chromatography and the instruments necessary for its application is available from Waters Associate Inc., Maple Street, Milford, Mass.]

In the following formulae Z is as hereinabove defined.

The 4-hydroxycyclopentenone racemates may be resolved into their component enantiomers (23) and (24) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpentanoic acid hydrochloride (to give 25), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (23) and (24). A useful procedure for the resolution of a 4-hydroxycyclopentenone racemate via an oxime such as (25) is described in the art [R. Pappo, P. Collins and C. Jung, *Tetrahedron Letters*, 943 (1973)]. The resolution of the hydroxycyclopentenone (23) wherein Z is

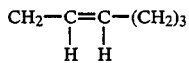

is described by Bruhn et al, *Tetrahedron Letters*, 235 (1976).

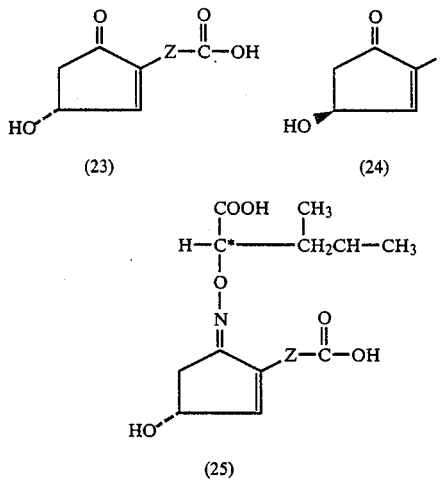

An alternative procedure for the preparation of the 4(R)-hydroxycyclopentenone enantiomers such as (23) involves as a key step the selective microbiological or chemical reduction of trione (26) to the 4(R)-hydroxycyclopentanedione (27). A wide variety of microorganisms are capable of accomplishing this asymmetric reduction, one of the most useful being *Dipodascus unincleatus*.

Conversion of hydroxycyclopentanedione (27) to an enol ether or enol ester, (28), E=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° C. to −15° C. Reduction of (28) with excess sodium bis(2-methoxyethoxy)aluminum hydride in a solvent such as tetrahydrofuran or toluene at low temperatures, such as −60° C. to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (29). The ester (29) after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih, et al., *J. A. C. S.*, 95, 1676 (1973); J. B. Heather, et al., *Tetrahedron Letters*, 2213 (1973); R. Pappo and P. W. Collins, *Tetrahedron Letters*, 2627 (1972); R. Pappo, P. Collins and C. Jung, *Ann. N.Y. Acad. Sci.*, 180, 64 (1971); C. J. Sih, et al., *J. A. C. S.*, 97, 865 (1975). For a description of the baker's yeast procedure see C. Sih, et al., *J. A. C. S.*, 94, 3643 (1972).

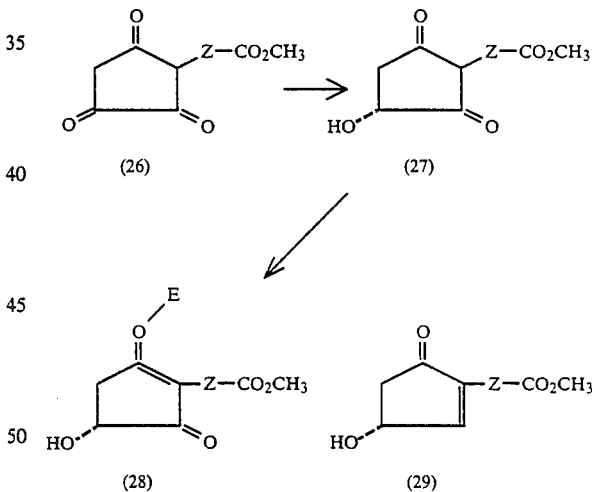

Procedures for the preparation of the requisite cyclopentanetriones (26) are well-established in the art and generally involve the treatment of an ω-1 oxo long chain ester (30) with methyl or ethyl oxalate and a base such as sodium methoxide in methanol, followed by treatment with dilute hydrochloric acid in aqueous methanol to effect the dealkoxalylation of the intermediate (31). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N.Y. Acad. Sci.*, 180, 64 (1971); C. J. Sih, et al., *J. A. C. S.*, 95, 1676 (1973) (see reference 7); and J. B. Heather, et al., *Tetrahedron Letters*, 2313 (1973) for pertinent background literature.

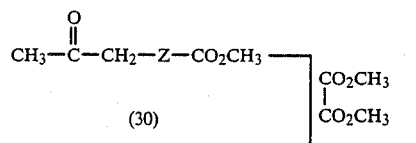

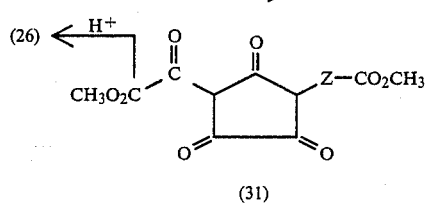

The intermediate keto esters (30) may be prepared by a variety of methods known to the art. One useful procedure is outlined below and involves alkylation of ethyl acetoacetate sodium salt (32) [in the usual manner with the appropriate side-chain precursor (33) X=Cl, Br, I, preferably Br or I] followed by decarbethoxylation and reesterification, all in the usual manner.

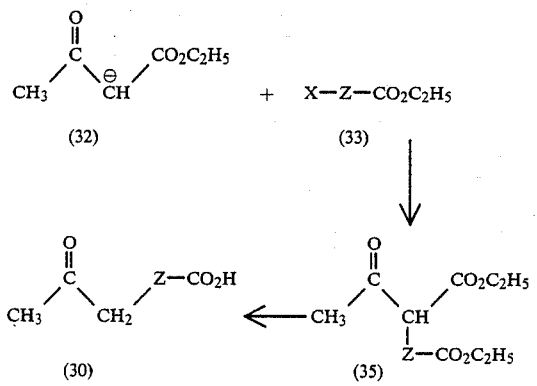

It is also possible to resolve the 4-hydroxycyclopentenone racemate (36) by microbiological means. Thus, treatment of the 4-O-alkanoyl or aroyl derivatives (37) $R_{12}$=aryl or alkyl) of racemate (36) (preferably the 4-O-acetyl and 4-O-propionyl derivatives) with an appropriate microorganism preferably a Saccharomyces species, e.g. 1375-143, affords preferential de-O-acylation of the 4(R)-enantiomer to give (23), which is then separated from the unreacted 4-(S)-O-acyl enantiomer (38) by chromatographic procedures. After separation, mild hydrolysis of the 4(S) derivative (38) provides the 4(S)-hydroxycyclopentenone (24) [See N. J. Marscheck and M. Miyano, *Biochimica et Biophysica Acta*, 316, 363 (1973) for related examples.]

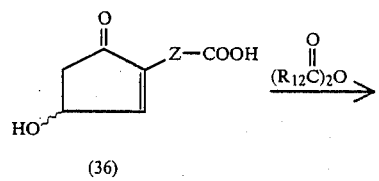

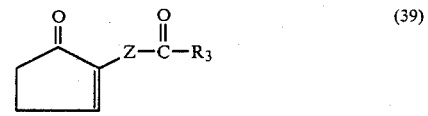

It is also possible to prepare the individual 4-hydroxycyclopentenones (23) and (24) directly by selective microbial hydroxylations of the corresponding 4-unsubstituted cyclopentenone (39). For example, with *Aspergillus niger* ATCC 9142; a selective 4(R)-hydroxylation of (39) [Z=$(CH_2)_6$] has been reported; for a literature example, see S. Kurozumi, T. Tora and S. Ishimoto, *Tetrahedron Letters*, 4959 (1973). Other organisms can also accomplish this hydroxylation.

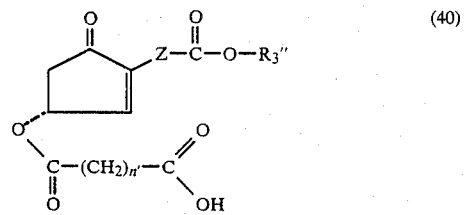

An alternate resolution procedure involves derivatization of the alcohol function of the racemic hydroxycyclopentenone to give ester-acid derivatives such as (40) wherein $R_3''$ is hydrogen or an alkyl group, n' is zero or two and Z is as hereinabove defined.

Such derivatives may be obtained from the corresponding free hydroxycyclopentenone by treatment in the usual manner with oxalyl chloride, succinyl chloride, succinic anhydride and the like. Treatment of the resulting acid or diacid ($R_3''$=hydrogen) with optically active amines e.g., l-(−)-α-methylbenzylamine, d-(+)-α-methylbenzylamine, brucine, dehydroabietylamine, strychnine, quinine, cinchonine, quinidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(S)- and 4(R)-hydroxycyclopentenone enantiomers (23) and (24) or their respective esters. Cleavage of the oxalate acid ester (40 n=0) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of succinate acid-ester see B. Goffinet, Ger. Offen. No. 2,263,080; *Chem. Abstracts*, 79, 78215$_z$ (1973).

Additional procedures, well-understood in the literature, for effecting the resolution of racemic prostenoic acids and esters of this invention are described below.

In these procedures a 9-oxo-11α,16(S)-16-vinyl-dihydroxy-5-cis, 13-trans-prostadienoic acid and its 9α-hydroxy derivative are used for illustrative purposes, it being understood, however, that the procedures are general and have applicability to the other products of this invention, particularly to those derivatives wherein the 11-position is not substituted with an oxy function.

Conversion of a 9α-hydroxy racemate (the component enantiomers are illustrated by (41) and (42) below) wherein the $C_{11}$ and $C_{16}$ hydroxy functions are preferentially blocked as tetrahydropyranyl or trialkylsilyl ethers and conversion of the diacid (e.g., 41) to a bis salt (e.g., 43) with an optically active amine (e.g., l-(−)-α-methylbenzylamine, D-(+)-α-methylbenzylamine, brucine, dehydroaebietylamine, styrychnine, quinine, cinchonine, cinchonindine, quinidine, ephedrine, deoxyephedrine, amphetamine, (+)-2-amino-1-butanol, (−)-2-amino-1-butanol and the like). The resulting diastereomers are then separated by fractional crystallization and the individual components are then converted by acidification and saponification to the individual optically active parent 9α-hydroxy enantiomers (41) and (42) oxidation of which after preferential blocking of the $C_{11}$ and $C_{16}$ hydroxy functions with tetrahydropyranyl or trialkylsilyl groups, provides the corresponding individual 9-oxo enantiomers (45) and (46) (For an appropriate literature procedure see E. W. Yankee, C. H. Lin and J. Fried, *Journ. Chem. Soc.*, 1972, 1120).

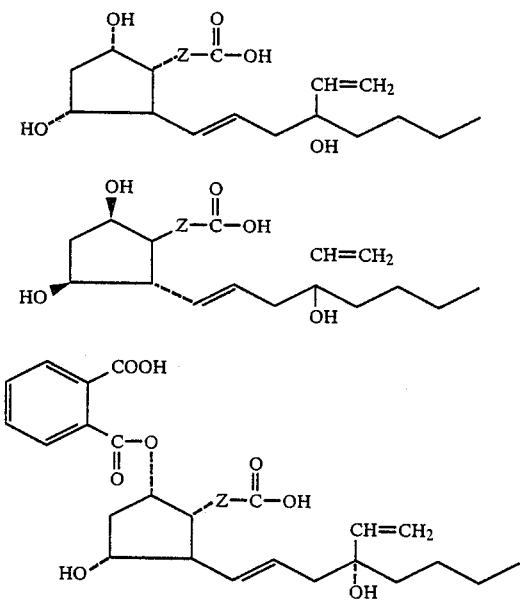

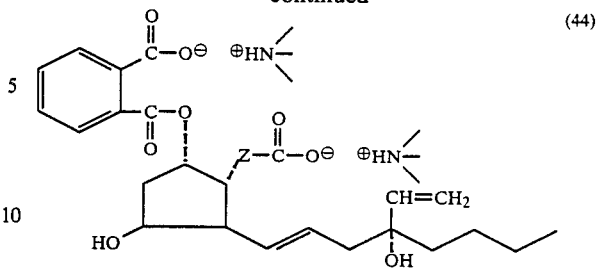

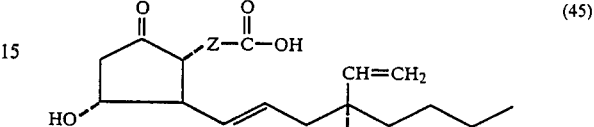

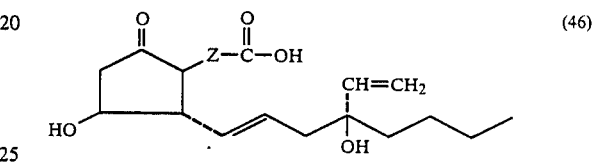

Another procedure involves conversion of the 9α-hydroxy racemate (as the prostenoic acid ester and with the $C_{11}$ and $C_{12}$ alcohol functions preferentially blocked as tetrahydropyranyl or trialkylsilyl ethers) to the diastereomeric carbamates with an optically active isocyanate, e.g., (+)-1-phenylethylisocyanate or (−)-1-phenylethylisocyanate, followed by deblocking. Separation of the diastereomers, for example (47) and (48) can be accomplished by fractional crystallization or by the usual chromatographic procedures, or if necessary by high speed liquid chromatography involving, if necessary, recycling techniques. Base-treatment of the individual diastereomeric carbamates affords the individual diastereomeric alcohols, for example (41) and (42).

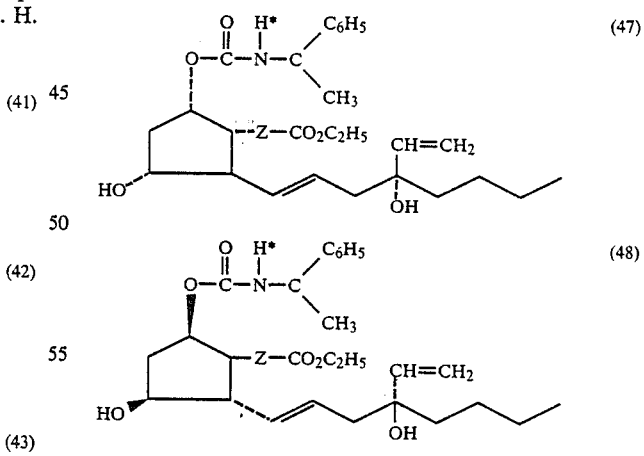

It is also possible to effect resolution of a 9α-hydroxy racemate, preferably as the prostenoate esters, by esterification of the 9α-hydroxy function (prior preferential blocking of $C_{11}$ and $C_{16}$ hydroxy functions as tetrahydropyranyl or trialkylsilyl ethers) with an optically active acid, via its acid chloride followed by deblocking the $C_{11}$ and $C_{16}$ alcohol groups. Suitable optically active acids include ω-camphoric acid, menthoxyacetic acid, 3α-acetoxy-Δ$^5$-etianic acid, (−)-α-methoxy-α-trifluoromethylphenylacetic acid and (+)-α-methoxy-α-trifluoromethylphenylacetic acid, and the like. The resulting diastereomeric esters, are then separated by fractional crystallization or by chromatographic techniques including, if necessary, the use of high speed liquid chromatography. Saponification of the individual diastereomers then provides the individual 9α-hydroxyprostenoic acid enantiomers (49) and (50).

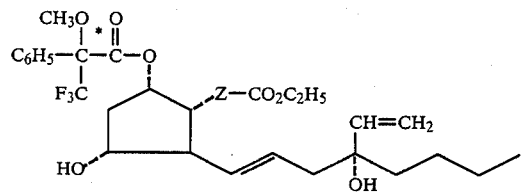
(49)

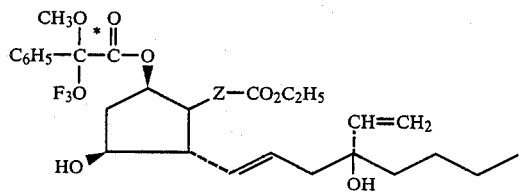
(50)

Another resolution procedure, less useful than the methods described above based on the 9α-hydroxy derivative but particularly applicable to 11-unsubstituted compounds of this invention, involves derivatization of the keto function of a racemic 9-oxoprostenoic acid or ester illustrated by (51) and (52) with the usual type of ketone derivatizing agent bearing an optically active center. The resulting mixture of diastereomeric derivatives can then be separated by fractional crystallization or by chromatography or, if necessary, by high speed liquid chromatography. The individual diastereomeric keto derivatives, for example (51) and (52) are then convertable to the individual 9-oxo enantiomers (45) and (46) by any of the usual cleavage techniques, provided that they are sufficiently mild so as not to disturb the sensitive 11-hydroxy-9-keto system. (This latter point is not a problem with 11-unsubstituted derivatives.) Ketone reduction of the 9-oxo-enantiomer as described hereinabove then provides the corresponding 9α-hydroxy or 9β-hydroxy enantiomer. Among the optically active reagents useful for ketone derivatization are l-α-aminoxy-α-methylpentanoic acid hydrochloride [E. Testa, et al., Helv. Chimica Acta, 47 (3), 766 (1973)], methylhydrazine, and 4-α-methylbenzylsemicarbazide. A useful procedure for the cleavage of oximes such as (51) and (52) involves treatment of the oxime at about 60° C. for about 4 hours in 1:2 aqueous-tetrahydrofuran buffered with ammonium acetate and containing titanium trichloride.

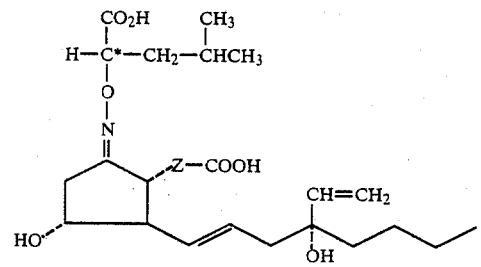
(51)

-continued

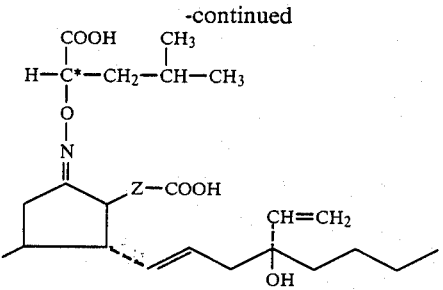
(52)

Other useful ketone derivatizing agents are optically active 1,2-glycols, e.g., D(−)-2,3-butanediol, or 1,2-dithiols, e.g., L(+)-2,3-butanedithiol. These are used to convert the 9-oxo derivative to 9,9-alkylenedioxa or 9,9-alkylenedithia derivatives, separation of diastereomers by chromatographic procedures followed by regeneration of the individual 9-oxo diastereomer by ketal cleavage all by procedures well-known in the art. Both ketalization and deketalization would have to be accomplished by procedures which would not disrupt the 11-oxo-9-keto system, which of course, is not a problem in the 11-unsubstituted series.

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various non-steroidal antiinflammatory agents (e.g., indomethacin, aspirin, and phenylbutazone), bronchodilators, antiinflammatory agents, abortifacients, agents for the induction of labor, agents for the induction of menses, fertility-controlling agents oestrus regulators for the use in animal husbandry with cattle and other domestic animals and central nervous system regulatory agents. Certain of the novel compounds of this invention possess utility as intermediates for the preparation of other of the novel compounds of this invention.

The ring system of certain of the novel compounds of this invention allow them to be characterized as follows:

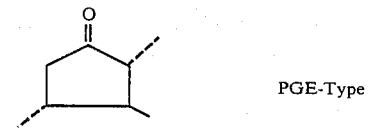
PGE-Type

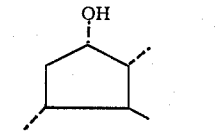
PGFα-Type

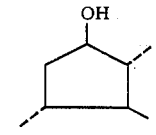
PGFβ-Type

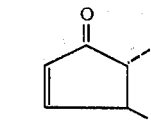
PGA-Type

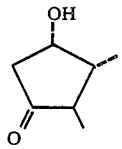

PGD-Type

The novel compounds of this invention possess the pharmacological activity described below as associated with the appropriate above-described prostaglandin type.

The known PGE, PGF$_\alpha$, PGF$_\beta$, PGA and PGD compounds are all potent in causing multiple biological responses even at low doeses. For example, PGE$_1$ and PGE$_2$ ae extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGF$_\alpha$ and PGF$_\beta$ compounds are additionally selective in that they are at most relatively very weak stimulants of smooth muscle. The 11-deoxy PGE compounds have a further advantage in that they are much more stable and have a longer "shelf-life" than the corresponding 11-hydroxy derivatives as described more fully hereinbelow.

Another advantage of the novel compounds of this invention, compared with the known prostaglandins, is that these novel compounds are adminsitered effectively, orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE$_1$, PGE$_2$, PGE$_3$ and dihydro-PGE$_1$, and the corresponding PGF$_\alpha$, PGF$_\beta$, and PGA, compounds, and their esters and pharmacologically acceptable salts, are extremely potent in causing various biological responses. For that reason, these compounds are useful for pharmacological purposes. See, for example, Bergstron, et al., Pharmacol. Rev., 20, 1 (1968), and references cited therein. A few of those biological responses are systemic arterial blood pressure lowering in the case of the PGE, PGF$_\beta$, and PGA compounds as measured, for example, in anesthetized (phenobarbital sodium) pentolinium-treated rats with indwelling aortic and right heart cannulas; pressor activity, similarly measured, for the PGF$_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg to about 10 mg per ml of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 g to about 500 μg per kg of body weight per minute, or in a total daily dose by injection or infusion in the range of about 0.1 mg to about 20 mg per kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE$_1$ and PGD$_2$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 mg to about 20 mg per kg of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 μg to about 50 μg per kg of body weight per minute until the desired effect is obtained. Subsequent doses are given by intravenous, subcutaneous, or intramuscular injection or infusion during puerperium in the range of 0.01 mg to 2 mg per kg of body weight per day, the exact dose depending on the age, weight, and condition of the patient or animal.

The PGE, PGFβ and PGA compounds are useful as hypotensive agents to reduce blood pressure in mammals including man. For this purpose, the compounds are administered by intravenous infusion at the rate about 0.01 μg to about 50 μg per kg of body weight per minute, or in a single or multiple doses of about 25 μg to 2500 μg per kg of body weight total per day.

The PGE, $PGF_\alpha$, and PGFβ compounds are useful in place of oxytocin to induce labor in pregnant female animals, including man, cows, sheep, pigs, at or near term or in pregnant animals with intrauterine death of the fetus from about 20 weeks to term. For this purpose, the compound is infused intravenously at a dose 0.01 μg to 50 μg per kg of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The PGE, PGFα, and PGFβ compounds are useful for controlling the reproductive cycle in ovulating female mammals, including humans and other animals. For that purpose, $PGF_2\alpha$, for example, is administered systemically at a dose level in the range of 0.01 mg to about 20 mg per kg of body weight, advantageously during a span of time starting approximately at the time of ovulation and ending approximately at the time of menses or just prior to menses. Additionally, expulsion of an embryo or fetus is accomplished by similar administration of the compound during the first third or the second third of the normal mammalian gestation period. Accordingly, they are useful as abortifacients. They are also useful for induction of menses during approximately the first two weeks of a missed menstrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severe impaired renal blood flow, for example, the hepatorena syndrom and early kidney transplant rejection. In case of excessive or inappropriate ADH antidiuretic hormone vasopressin secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing 2 to 2000 μg/ml of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example hydrocortisone, prednisolone, methylprednisolone, and fluoroprednisoline, each of those being used in combination at the usual concentrations suitable for its use alone.

The novel compounds of this invention induce the biological responses described hereinabove as associated with its particular prostaglandin type. These novel compounds are accordingly used for the above-described corresponding purposes.

The novel PGE, PGFβ and PGA compounds of this invention are also useful as bronchodialtors for the treatment of asthma and chronic bronchitis. As such they may be conveniently administered by inhalation of aerosol sprays prepared in a dose range of about 10 μg to about 10 mg/ml of a pharmacologically suitable liquid vehicle. Relative to the natural prostaglandins, the PGE compounds in particular have the significant advantage of inducing prolonged effects.

The invention will be described in greater detail in conjunction with the following specific examples.

EXAMPLE 1

Preparation of 4-Trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine, dried over magnesium sulfate, and concentrated. Distillation of the residue gives a colorless liquid, b.p. 38° (0.2 mm).

EXAMPLE 2

Preparation of 1-Iodo-4-trimethylsiloxy-trans-1-octene

To a stirred solution of 0.20 moles of freshly prepared bis-(3-methyl-2-butyl)borane in 300 ml of tetrahydrofuran at 0°–5° C. is added dropwise a solution of 19.8 g of 4-trimethylsiloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°–40° C. and then poured into 2 liters of 15% sodium hydroxide. The resulting mixture is treated immediately with a solution of 140 g of iodine in 300 ml of tetrahydrofuran. After 0.5 hour the organic phase is separated and the aqueous phase is extracted with ether. The combined organic layers are washed with water, sodium thiosulfate solution, and brine; dried over magnesium sulfate; and concentrated to give an oil, pmr spectrum (CDCl$_3$): 6.2 (d, IC$\underline{H}$=) and 6.7 (quintuplet, =C$\underline{H}$—).

EXAMPLE 3

Preparation of 4-Hydroxy-1-iodo-trans-1-octene

A 23 g portion of 1-iodo-4-trimethylsiloxy-trans-1-octene is dissolved in a mixture of 200 ml of glacial acetic acid, 100 ml of tetrahydrofuran, and 50 ml of water. After solution occurs, toluene is added and the mixture is evaporated. The resulting oil is chromatographed on silica gel with hexane progressively enriched in benzene followed by acetone to give 16 g of an oil, pmr spectrum (CDCl$_3$): 3.69 (m, C$\underline{H}$OH) and 2.3 (s, O$\underline{H}$).

EXAMPLE 4

Preparation of 4-Oxo-1-iodo-trans-1-octene

To a stirred suspension of 6.15 g of pyridinium chlorochromate (Tetrahedron Letters, 1975, 2647) in 20 ml of methylene chloride is added 450 mg of sodium acetate. After 5 minutes a solution of 3.64 g of 4-hydroxy-1-iodo-trans-1-octene in 15 ml of methylene chloride is added in one portion. The dark mixture is stirred at room temperature for 75 minutes, diluted with 50 ml of ether, and decanted. The solid sludge is washed repeatedly with ether and decanted. The combined solutions are percolated through Florisil. The solution is concentrated to give an orange liquid, pmr spectrum (CDCl$_3$): 3.20 (d, J=7 cps, =CHC$\underline{H_2}$CO).

EXAMPLE 5

Preparation of 4-Hydroxy-4-vinyl-1-iodo-trans-1-octene

To a stirred solution of 7.8 ml of vinyl magnesium chloride (2.3M in tetrahydrofuran), at −25° C. is added a solution of 3.55 g of 4-oxo-1-iodo-trans-1-octene in 20 ml of tetrahydrofuran during 15 minutes. After the addition, the solution is stirred at −20° C. to −15° C. for 30 minutes. The reaction is quenched with a mixture of hexane and ice. The aqueous phase is separated and extracted with additional hexane. The combined hexane extracts are washed successively with water and brine. The solution is dried over magnesium sulfate and concentrated. The residue is subjected to dry column chromatography on silica gel with benzene as developing solvent to give a liquid, pmr spectrum (CDCl3): 5.2 (m, terminal C$\underline{H_2}$), 5.83 (q, C$\underline{H}$=CH$_2$), 6.13 (d, IC$\underline{H}$=), and 6.52 (m, ICM=C$\underline{H}$).

EXAMPLE 6

Preparation of 4-Trimethylsiloxy-4-vinyl-1-iodo-trans-1-octene

To a stirred solution of 456 mg of 4-hydroxy-4-vinyl-1-iodo-trans-1-octene and 320 mg of imidazole in 1.0 ml of dimethylformamide is added 0.23 ml of chlorotrimethylsilane during 3 minutes. The mixture is stirred at room temperature for 22 hours and partitioned with a mixture of cold hexane and water. The hexane layer is washed repeatedly with water and then brine, dried over magnesium sulfate, and concentrated to give an oil, pmr spectrum (CDCl$_3$): 0.13 (s, trimethylsiloxy group) and 2.32 (d, =CHC$\underline{H_2}$).

EXAMPLE 7

Preparation of 9-Oxo-11α,16-dihydroxy-16-vinyl-13-trans-prostenoic Acid

To a stirred solution of 555 mg of 4-trimethylsiloxy-4-vinyl-1-iodo-trans-1-octene in 2 ml of ether is added a solution of t-butyllithium in pentane (1.6M) during 10 minutes at −78° C. The solution is stirred at −78° C. for 1.5 hours and at −50° C. for 30 minutes to provide the 1-lithio-trans-alkene.

In a separate flask a mixture of 0.21 g of 1-copper-(I)-1-pentyne, 0.70 ml of hexamethylphosphorous triamide, and 2 ml of ether is stirred until a clear solution is obtained. This solution is added during 10 minutes to the stirred 1-lithio-trans-alkene solution at −78° C. The solution is stirred for 2 hours at −78° C. and then treated with a solution of 580 mg of 4-(trimethylsiloxy)-2-(6-carbotrimethylsiloxyhexyl)cyclopent-2-en-1-one in 3 ml of ether during 10 minutes. After 10 minutes at −78° C. the solution is stirred at −40° C. to −50° C. for one hour and at −35° C. to −30° C. for one hour. The solution is cooled to −50° C., poured into 100 ml of saturated ammonium chloride solution, and diluted with ether. The organic phase is separated, washed successively with water and dilute hydrochloric acid, and filtered through diatomaceous earth. The filtrate is washed successively with water and brine and dried over magnesium sulfate. Evaporation of solvent affords the crude bis-trimethylsilyl ether as an oil.

This oil is treated with a solution prepared from 10 ml of glacial acetic acid, 5 ml of tetrahydrofuran, and 2.5 ml of water. The mixture is stirred at room temperature for 30 minutes and diluted with 50 ml of toluene. After concentration at 33° C. in vacuo, the residue is subjected to chromatography on silica gel with 1% acetic acid in ethyl acetate to provide an oil, pmr spectrum (CDCl$_3$): 4.08 (q, 11β—$\underline{H}$), 5.1 (m, terminal C$\underline{H_2}$), 5.57 (m, trans—C$\underline{H}$=C$\underline{H}$), and 5.89 (m, C$\underline{H}$=CH$_2$).

EXAMPLE 8

Preparation of n-butyl cyclopropyl ketone

To a vigorously-stirred solution of 31.0 g of cyclopropanecarboxylic acid in 330 ml of ether is added a solution of n-butyllithium (748 mmoles) in ca. 750 ml. of 2:1 ether-hexane during 1 hour at 5°–10° C. The resulting suspension is diluted with 300 ml of ether and stirred at room temperature for 2 hours and at reflux for 2 hours. The mixture is cooled and poured into several portions of 1:1 ice—4N hydrochloric acid. The ethereal phases are combined and washed with brine, sodium carbonate solution, and brine. The extract is dried over magnesium sulfate and concentrated. The residue is distilled to provide a liquid, b.p. 102°–104° C. (80 mm), pmr spectrum (CDCl$_3$): δ 2.55 (triplet, —CH$_2$CO—).

EXAMPLE 9

Preparation of 4-Cyclopropyl-4-hydroxy-1-octyne

To a stirred, refluxing suspension of amalgam prepared from 6.2 g of magnesium and 50 mg of mercuric chloride suspended in 60 ml of ether is added a solution of a mixture of 30.4 g of n-butyl cyclopropyl ketone (Example 8) and 29.8 g of propargyl bromide in 65 ml of ether during 60 minutes. After reaction at reflux temperature for an additional 30 minutes, the mixture is cooled to 0° and treated with 35 ml of saturated ammonium chloride. The mixture is diluted with ether and filtered through Celite. The filtrate is washed with brine, dried over potassium carbonate, and concentrated. The residue is distilled to provide a liquid, b.p. 93°–94° C. (12 mm), pmr spectrums (CDCl$_3$): δ 0.43 (cyclopropyl hydrogens), 2.07 (triplet, $\underline{H}$C≡C), and 2.44 (doublet, C≡CC$\underline{H_2}$).

EXAMPLE 10

Preparation of 4-Cyclopropyl-4-trimethylsiloxy-1-octyne

To a stirred solution of 27.8 g. of 4-cyclopropyl-4-hydroxy-1-octyne (Example 9) and 33.3 g. of imidazole in 130 ml of dimethylformamide at 5° C. is added 24 ml. of chlorotrimethylsilane during 5 minutes. The solution is stirred at ambient temperature for 17 hours and then partitioned with 600 ml of hexane and 250 ml of ice-water. The hexane phase is separated and washed successively with water and brine. The solution is dried over magnesium sulfate and evaporated to give a liquid, p.m.r. spectrum (CDCl$_3$): β 0.12 (singlet, trimethylsiloxy group), 2.02 (triplet, $\underline{H}$C≡C), and 2.45 (doublet, C≡C$\underline{H_2}$).

EXAMPLE 11

Preparation of 4-Cyclopropyl-4-trimethylsiloxy-1-(tri-n-butylstannyl)-trans-1-octene A stirred mixture of 23.8 g of 4-cyclopropyl-4-trimethylsiloxy-1-octyne (Example 10), 28 ml of tri-n-butyltin hydride, and 50 mg of azobisisobutyronitrile under nitrogen is heated to 85° C. After the resulting exothermic reaction subsides the mixture is heated at 130° C. for 1 hour. The crude product is evaporatively distilled to give a liquid, p.m.r. spectrum (CDCl$_3$): δ 0.10 (trimethylsiloxy group), 2.33 (doublet, =CHC$\underline{H_2}$), and 6.02 (vinyl hydrogens).

EXAMPLES 12–13

In the manner of Example 8 the following cyclopropyl alkyl ketones of Table 1 are prepared by reaction of the appropriate alkyllithium with cyclopropanecarboxylic acid.

TABLE 1

| Example | Alkyllithium | Product Cyclopropyl Alkyl Ketone |
| --- | --- | --- |
| 12 | n-propyllithium | cyclopropyl n-propyl ketone |
| 13 | n-amyllithium | n-amyl cyclopropyl ketone |

TABLE 1-continued

| Example | Alkyllithium | Product Cyclopropyl Alkyl Ketone |
| --- | --- | --- |
| 14 | n-hexyllithium | cyclopropyl n-hexyl ketone |

EXAMPLES 15–18

The following vinyl ketones of Table 2 below are prepared by reaction of vinyllithium with the requisite carboxylic acids of the table according to a procedure well-known in the art [J. C. Floyd, Tetrahedron Letters, 2877 (1974)].

TABLE 2

| Example | Carboxylic Acid | Product Alkyl Vinyl Ketone |
| --- | --- | --- |
| 15 | n-butyric acid | n-propyl vinyl ketone |
| 16 | n-valeric acid | n-butyl vinyl ketone |
| 17 | n-hexanoic acid | n-amyl vinyl ketone |
| 18 | n-heptanoic acid | n-hexyl vinyl ketone |

EXAMPLES 18a–20

In the manner of Example 9 the following 4-substituted-1-alkyn-4-ols are prepared by reaction of propargyl magnesium bromide with the ketones of Table 3 below.

TABLE 3

| Example | Starting Ketones of Example | Product 4-Substituted-1-alkyn-4-ol |
| --- | --- | --- |
| 18a | 12 | 4-cyclopropyl-4-hydroxy-1-heptyne |
| 18b | 13 | 4-cyclopropyl-4-hydroxy-1-nonyne |
| 18c | 14 | 4-cyclopropyl-4-hydroxy-1-decyne |
| 18d | 15 | 4-hydroxy-4-vinyl-1-heptyne |
| 19 | 17 | 4-hydroxy-4-vinyl-1-nonyne |
| 20 | 18 | 4-hydroxy-4-vinyl-1-1-decyne |

EXAMPLES 21–25

In the manner of Example 10 the following 4-substituted-1-alkyn-4-ols of Table 4 below are converted to their corresponding trimethylsilyl ethers.

TABLE 4

| Example | 1-Alkyn-4-ol of Example | Product 4-Trimethylsiloxy-1-alkyne |
| --- | --- | --- |
| 21 | 18a | 4-cyclopropyl-4-trimethylsiloxy-1-heptyne |
| 22 | 18b | 4-cyclopropyl-4-trimethylsiloxy-1-nonyne |
| 23 | 18c | 4-cyclopropyl-4-trimethylsiloxy-1-decyne |
| 24 | 18d | 4-trimethylsiloxy-4-vinyl-1-heptyne |
| 25 | 19 | 4-trimethylsiloxy-4-vinyl-1-nonyne |
| 26 | 20 | 4-trimethylsiloxy-4-vinyl-1-decyne |

EXAMPLES 27–32

In the manner of Example 11 the following 1-(tri-n-butylstannyl)-4-substituted-4-trimethylsiloxy-trans-1-alkenes are prepared by reaction of tri-n-butyltin hydride with the precursor 1-alkynes of Table 5 below.

TABLE 5

| Example | Starting 1-Alkyns of Example | Product 1-(tri-n-butyl-stannyl)-1-trans-alkene |
|---|---|---|
| 27 | 21 | 1-(tri-n-butylstannyl)-4-cyclopropyl-4-trimethylsiloxy-trans-1-heptene |
| 28 | 22 | 1-(tri-n-butylstannyl)-4-cyclopropyl-4-trimethylsiloxy-trans-1-nonene |
| 29 | 23 | 1-(tri-n-butylstannyl)-4-cyclopropyl-4-trimethylsiloxy-trans-1-decene |
| 30 | 24 | 1-(tri-n-butylstannyl)-4-vinyl-4-trimethylsiloxy-trans-1-heptyns |
| 31 | 25 | 1-(tri-n-butylstannyl)-4-vinyl-4-trimethylsiloxy-trans-1-nonene |
| 32 | 26 | 1-(tri-n-butylstannyl)-4-vinyl-4-trimethylsiloxy-trans-1-decene |

EXAMPLE 33

Preparation of 9-oxo-11α,16-dihydroxy-16-cyclopropyl-5-cis,13-trans-prostadienoic acid To a stirred solution of 11.54 g of 4-cyclopropyl-4-trimethylsiloxy-1-(tri-n-butylstannyl)-trans-1-octene (Example 11) in 10 ml of tetrahydrofuran at −78° C. is added 9.1 ml of 2.4M n-butyllithium in hexane during 10 minutes. The resulting solution is stirred at −70° C. for 10 minutes, at −40° C. for 1 hour, and at −40° C. to −30° C. for 40 minutes. To the stirred solution at −78° C. is added a solution prepared from 2.84 g of copper pentyne, 10.8 ml of tri-n-butyl-phosphine, and 25 ml of ether. The resulting solution is stirred at −78° C. for 2 hours and then treated during 10 minutes with a solution of 6.03 g of 2-(6-trimethylsiloxycarbonyl-2'-cis-hexenyl-4-trimethylsiloxycyclopent-2-en-1-one Table 6, Ref. A in 20 ml of ether. After 10 minutes the solution is stirred at −50° C. to −40° C. for 1 hour then at −40° C. to −30° C. for 50 minutes. The solution is recooled to −50° C. and poured into a stirred mixture of 600 ml of saturated ammonium chloride and 300 ml of ether. The organic phase is separated and washed successively with dilute hydrochloric acid, water and brine.

The residue obtained after evaporation of solvent is treated with 120 ml of gl. acetic acid, 60 ml of tetrahydrofuran, and 30 ml of water, and the mixture is stirred at room temperature for 30 minutes, diluted with 150 ml of toluene, and concentrated. The residue is purified by dry column chromatography on silica gel with 1% acetic acid in ethyl acetate to provide an oil, p.m.r. spectrum (acetone-d6): δ 0.26 (multiplet, cyclopropyl hydrogens) and 4.12 (quartet, C$\underline{\text{H}}$OH).

EXAMPLE 34-49

The product 9-oxo-11α,16-dihydroxy-prostadienoic or prostenoic acids of Table 6 below are obtained by the procedure described in Example 33. In accordance with the process described therein, the starting 1-(tri-n-butyl-stannyl)-4-trimethylsiloxy-trans-1-alkenes listed in Table 6 are treated with n-butyllithium to provide the corresponding trans-1-alkenyl lithium derivative which on treatment with copper pentyne-tri-n-butylphosphine complex furnish the corresponding trans-1-alkenylcuprates, which in turn are treated with the 4-oxycyclopent-2-en-1-ones listed in the table. The resulting 9-oxo-11α,16-bis(trimethylsiloxy)-prostadienoic or prostenoic acid trimethylsilyl ester is hydrolyzed to the listed products by treatment with acetic acid-tetrahydrofuran-water.

TABLE 6

| Example | Starting 4-oxy-cyclopent-2-en-1-one | Starting 1-(tri-n-butylstannyl)-4-trimethylsiloxy-trans-1-alkene of Example | Product 9-oxo-11α,16-dihydroxy-prostadienoic or prostenoic acid. |
|---|---|---|---|
| 34 | Example 126 | 27 | 9-oxo-11α,16-cyclopropyl-20-nor-13-trans prostenoic acid. |
| 35 | Example 126 | 28 | 9-oxo-11α,16-dihydroxy-16-cyclopropyl-20-methyl-13-trans-prostenoic acid |
| 36 | Example 126 | 29 | 9-oxo-11α,16-dihydroxy-16-cyclopropyl-20-ethyl-13-trans-prostenoic acid |
| 37 | Example 126 | 30 | 9-oxo-11α,16-dihydroxy-16-vinyl-20-nor-13-trans-prostenoic acid. |
| 38 | Example 126 | 31 | 9-oxo-11α,16-dihydroxy-16-vinyl-20-methyl-13-trans-prostenoic acid. |
| 39 | Example 126 | 32 | 9-oxo-11α,16-dihydroxy-16-vinyl-20-ethyl-13-trans-prostenoic acid. |
| 40 | Example 126 | 11 | 9-oxo-11α,16-dihydroxy-16-cyclopropyl-13-trans-prostenoic acid. |
| 41 | A | 27 | 9-oxo-11α,16-dihydroxy-16-cyclopropyl-20-nor-5-cis,13-trans-prostadienoic acid |
| 42 | A | 28 | 9-oxo-11α,16-dihydroxy-16-cyclopropyl-20-methyl-5-cis,13-trans-prostadienoic acid |
| 43 | A | 29 | 9-oxo-11α,16-dihydroxy-16-cyclopropyl-20-ethyl-5-cis,13-trans-prostadienoic acid |
| 44 | A | 30 | 9-oxo-11α,16-dihydroxy-16-vinyl-20-nor-5-cis,13- |

TABLE 6-continued

| Example | Starting 4-oxy-cyclopent-2-en-1-one | Starting 1-(tri-n-butylstannyl)-4-trimethylsiloxy-trans-1-alkene of Example | Product 9-oxo-11α,16-dihydroxy-prostadienoic or prostenoic acid. |
|---|---|---|---|
| 45 | A | 31 | trans-prostadienoic acid 9-oxo-11α,16-dihydroxy-16-vinyl-20-methyl-5-cis,13-trans-prostadienoic acid |
| 46 | A | 32 | 9-oxo-11α,16-dihydroxy-16-vinyl-20-ethyl-5-cis,13-trans-prostadienoic acid |
| 47 | A | 6 (by procedure of Ex. 7) | 9-oxo-11α,16-dihydroxy-16-vinyl-5-cis,13-trans-prostadienoic acid. |
| 48 | Example 127 | 6 | 1-9-oxo-11α,16-dihydroxy-16-vinyl-13-trans-prostenoic acid methyl ester |
| 49 | Example 128 | 11 | 1-9-oxo-11α,16-dihydroxy-16-cyclopropyl-5-cis-13-trans-prostadienoic acid methyl ester |
| 49A | Example 129 | 6 | 9-oxo-11α,16-dihydroxy-16-vinyl-5-cis,13-trans-2a,2b-bishomoprostadienoic acid |
| 49B | Example 129 | 11 | 9-oxo-11α,16-dihydroxy-16-cyclopropyl-5-cis,13-trans-2a,2b-bishomoprostadienoic acid |
| 49C | Example 129A | 11 | 9-oxo-11α,16-dihydroxy-16-cyclopropyl-13-trans-3-oxa-prostenoic acid |
| 49D | Example 129B | 6 | 9-oxo-11α,16-dihydroxy-16-vinyl-13-trans-3-oxa-prostenoic acid. |

A = 4-trimethylsiloxy-2-(6-carbotrimethylsiloxy)-2-cis-hexenyl)-cyclopent-2-en-1-one (U.S. Pat. No. 3,873,607, Example 1125).

EXAMPLE 50

Preparation of 9α,11α,16-trihydroxy-16-cyclopropyl-5-cis,13-trans-prostadienoic acid To a stirred solution of 785 mg. of 9-oxo-11α,16-dihydroxy-16-cyclopropyl-5-cis,13-trans-prostadienoic acid (Example 33) in 12 ml. of tetrahydrofuran at −70° is added 12 ml. of a 0.5M solution of lithium perhydro-9b-boraphenalyl hydride in tetrahydrofuran. The solution is stirred at −78° C. for 30 minutes, warmed to 0° during 15 minutes, and treated with 0.6 ml. of water. The mixture is partitioned with etherpotassium carbonate solution. The aqueous phase is acidified with hydrochloric acid and extracted with ethyl acetate. The extract is washed with water and brine, dried over magnesium sulfate, and concentrated. The resulting residue is subjected to dry column chromatography on silica gel with 1% acetic acid in ethyl acetate to provide a viscous oil, pmr spectum (acetone-d$_6$): δ 3.90 (multiplet, 11β-H) and 4.10 (multiplet, 9β-H)

EXAMPLES 51–67

Reduction of the 9-oxo-derivatives listed in the Table 7 below with lithium perhydro-9-b-boraphenalyl hydride by the method described in Example 50 provides the product 9α-hydroxy-prostadienoic and prostenoic acids of the table.

TABLE 7

| Example | Starting 9-oxo-prostadienoic or prostenoic acid of Example | Product 9α,11α,16-trihydroxy-prostadienoic or prostenoic acid |
|---|---|---|
| 51 | 34 | 9α,11α,16-trihydroxy-16-cyclopropyl-20-nor-13-trans-prostenoic acid |
| 52 | 35 | 9α,11α,16-trihydroxy-16-cyclopropyl-20-methyl-13-trans-prostenoic acid |
| 53 | 36 | 9α,11α,16-trihydroxy-16-cyclopropyl-20-ethyl-13-trans-prostenoic acid |
| 54 | 37 | 9α,11α,16-trihydroxy-16-vinyl-20-nor-13-trans-prostenoic acid |
| 55 | 38 | 9α,11α,16-trihydroxy-16-vinyl-20-methyl-13-trans-prostenoic acid |
| 56 | 39 | 9α,11α,16-trihydroxy-16-vinyl-20-ethyl-13-trans-prostenoic acid |
| 57 | 40 | 9α,11α,16-trihydroxy-16-cyclopropyl-13-trans-prostenoic acid |
| 58 | 41 | 9α,11α,16-trihydroxy-16-cyclopropyl-20-nor-5-cis,13-trans-prostadienoic acid |
| 59 | 42 | 9α,11α,16-trihydroxy-16-cyclopropyl-20-methyl-5-cis,13-trans-prostadienoic acid |
| 60 | 43 | 9α,11α,16-trihydroxy-16-cyclopropyl-20-ethyl-5-cis,13-trans-prostadienoic acid |
| 61 | 44 | 9α,11α,16-trihydroxy-16-vinyl-20-nor-5-cis,13-trans-prostadienoic acid |
| 62 | 45 | 9α,11α,16-trihydroxy-16-vinyl-20-methyl-5-cis,13-trans-prostadienoic acid |
| 63 | 46 | 9α,11α,16-trihydroxy-16-vinyl-20-ethyl-5-cis,13-trans-prostadienoic acid |
| 64 | 47 | 9α,11α,16-trihydroxy-16-vinyl-5-cis,13-trans-prostadienoic acid |
| 65 | 7 | 9α,11α,16-trihydroxy-16-vinyl- |

TABLE 7-continued

| Example | Starting 9-oxo-prostadienoic or prostenoic acid of Example | Product 9α,11α,16-trihydroxy-prostadienoic or prostenoic acid |
|---|---|---|
| 66 | 48 | 1-9α,11α,16-trihydroxy-16-vinyl-13-trans-prostenoic acid methyl ester |
| 67 | 49 | 1-9α,11α,16-trihydroxy-16-cyclopropyl-5-cis-13-trans-prostadienoic acid methyl ester |
| 67A | 49A | 9α,11α,16-trihydroxy-16-vinyl-5-cis-13-trans-2a,2b-bishomo-prostadienoic acid. |
| 67B | 49B | 9α,11α,16-trihydroxy-16-cyclopropyl-5-cis,13-trans-2a,2b-bis-homoprostadienoic acid. |
| 67C | 49C | 9α,11α,16-trihydroxy-16-cyclopropyl-13-trans-3-oxa-prostenoic acid |
| 67D | 49D | 9α,11α,16-trihydroxy-16-vinyl-13-trans-3-oxa-prostenoic acid |

EXAMPLE 68

Preparation of 9-oxo-16-hydroxy-16-vinyl-5-cis,10,13-trans-prostatrienoic acid

To a stirred solution of 0.28 g of 9-oxo-11α,16-dihydroxy-16-vinyl-5-cis,13-trans-prostadienoic acid (Example 47) in 25 ml of pyridine is added 2.7 ml of acetic anhydride. After standing for 5 hours at room temperature, the solution is stirred with a mixture of ethyl acetate and 1M aqueous sodium bisulfate at 0°. The ethyl acetate layer is washed with brine and concentrated in the presence of toluene.

The residue, consisting of crude 9-oxo-11α-acetoxy-16-hydroxy-16-vinyl-5-cis,13-trans-prostadienoic acid, is dissolved in 20 ml of methanol with 1.2 g of potassium acetate. After standing for 18 hours at room temperature, the solution is partitioned with ethyl acetate and brine. The organic phase is washed with brine, dried over magnesium sulfate, and concentrated. The residue is purified by partition chromatography on Celite with the system heptane-dochloromethane-methanol-water (80:20:15:6) to give an oil, pmr spectrum (acetone-d$_6$): 3.35 (multiplet, 12-H), 6.10 (quartet, 10-H), and 7.55 (quartet, 11-H).

EXAMPLES 69–83b

Treatment of the 9-oxo-11α,16-dihydroxy prostadienoic or prostenoic acids of Table 8 below with acetic anhydride in pyridine followed by potassium acetate in methanol according to Example 68 furnishes the product 9-oxo-16-hydroxy-Δ$^{10}$-prostadienoic or prostatrienoic acids of the table.

TABLE 8

| Example | Starting 9-oxo-11α-16-dihydroxy prostadienoic or prostenoic acid of Example | Product 9-oxo-16-hydroxy-prostadienoic or prostatrienoic acid |
|---|---|---|
| 69 | 34 | 9-oxo-16-hydroxy-16-cyclopropyl-20-nor-10,13-trans-prostadienoic acid |
| 70 | 35 | 9-oxo-16-hydroxy-16-cyclopropyl-20-methyl-10,13-trans-prostadienoic acid |
| 71 | 36 | 9-oxo-16-hydroxy-16-cyclopropyl-20-ethyl-10,13-trans-prostadienoic acid |
| 72 | 37 | 9-oxo-16-hydroxy-16-vinyl-20-nor-10,13-trans-prostadienoic acid |
| 73 | 38 | 9-oxo-16-hydroxy-16-vinyl-20-methyl-10,13-trans-prostadienoic acid |
| 74 | 39 | 9-oxo-16-hydroxy-16-vinyl-20-ethyl-10,13-trans-prostadienoic acid |
| 75 | 40 | 9-oxo-16-hydroxy-16-cyclopropyl-10,13-trans-prostadienoic acid |
| 76 | 41 | 9-oxo-16-hydroxy-16-cyclopropyl-20-nor-5-cis,10,13-trans-prostatrienoic acid |
| 77 | 42 | 9-oxo-16-hydroxy-16-cyclopropyl-20-methyl-5-cis,10,13-trans-prostatrienoic acid |
| 78 | 43 | 9-oxo-16-hydroxy-16-cyclopropyl-20-ethyl-5-cis,10,13-trans-prostatrienoic acid |
| 79 | 44 | 9-oxo-16-hydroxy-16-vinyl-20-nor-5-cis,10,13-trans-prostatrienoic acid |
| 80 | 45 | 9-oxo-16-hydroxy-16-vinyl-20-methyl-5-cis,10,13-trans-prostatrienoic acid |
| 81 | 46 | 9-oxo-16-hydroxy-16-vinyl-20-ethyl-5-cis,10,13-trans-prostatrienoic acid |
| 82 | 47 | 9-oxo-16-hydroxy-16-vinyl-5-cis,10,13-trans-prostatrienoic acid |
| 83 | 33 | 9-oxo-16-hydroxy-16-cyclopropyl-5-cis,10,13-trans-prostatrienoic acid |
| 83a | 49A | 9-oxo-16-hydroxy-16-vinyl-5-cis,10,13-trans-2a,2b-bishomoprostatrienoic acid |
| 83b | 49B | 9-oxo-16-hydroxy-16-cyclopropyl-5-cis,10,13-trans-2a,2b-bishomo-prostatrienoic acid |
| 83c | 49C | 9-oxo-16-hydroxy-16-cyclopropyl-10,13-trans-3-oxa-prostadienoic acid |
| 83d | 49D | 9-oxo-16-hydroxy-16-vinyl-10,13-trans-3-oxa-prostadienoic acid |

EXAMPLES 84–91

Treatment of the cyclopentenone alkyl esters of Table 9 below with the cuprate derived from 1-(tri-n-butylstannyl-4-cyclopropyl-4-trimethylsiloxy-trans-1-octene (Example 11) by the procedure of Example 33 or with the cuprate derived from 4-trimethylsiloxy-4-vinyl-1-iodo-trans-1-octene (Example 6) by the procedure of Example 7 followed by removal of the trimethylsilyl group according to the procedure of Example 33 provides the 16-substituted-16-hydroxy prostenoic alkyl esters of the Table.

TABLE 9

| Example | Starting Cyclopentenone Alkyl Ester | Starting 1-(tri-n-butylstannyl-4-trimethylsiloxy-trans-1-alkene of Example | Product 16-substituted-16-hydroxy prostadienoic or prostenoic acid alkyl ester |
|---|---|---|---|
| 84 | 2-(6-carbomethoxy-2-cis-hexenyl)cyclopent- | 11 | methyl 9-oxo-16-hydroxy-16-cyclopropyl-5-cis,13-trans- |

TABLE 9-continued

| Example | Starting Cyclopentenone Alkyl Ester | Starting 1-(tri-n-butylstannyl-4-trimethylsiloxy-trans-1-alkene of Example | Product 16-substituted-16-hydroxy prostadienoic or prostenoic acid alkyl ester |
|---|---|---|---|
| | 2-en-1-one (U.S. Pat. No. 3,873,607) | | prostadienoate |
| 85 | 2-(6-carbomethoxy-2-cis-hexenyl)cyclopent-2-en-1-one (U.S. Pat. No. 3,873,607) | 6 | methyl 9-oxo-16-hydroxy-16-vinyl-5-cis,13-trans-prostadienoate |
| 86 | 2-(6-carbethoxyhexyl)-2-cyclopentenone (U.S. Pat. No. 3,873,607) | 11 | ethyl 9-oxo-16-hydroxy-16-cyclopropyl-13-trans-prostenoate |
| 87 | 2-(6-carbethoxyhexyl)-2-cyclopentenone (U.S. Pat. No. 3,873,607) | 6 | ethyl 9-oxo-16-hydroxy-16-vinyl-13-trans-prostenoate |
| 88 | 2-(6-carbethoxy-5-thiahexyl)-2-cyclopentenone (U.S. Pat. No. 3,873,607) | 6 | ethyl 9-oxo-16-hydroxy-16-vinyl-3-thia-13-trans-prostenoate |
| 89 | 2-(6-carbethoxy-5-thiahexyl)-2-cyclopentenone (U.S. Pat. No. 3,873,607) | 11 | ethyl 9-oxo-16-hydroxy-16-cyclopropyl-3-thia-13-trans-prostenoate |
| 90 | 2-(6-carbethoxy-5-oxahexyl)-2-cyclopentenone (U.S. Pat. No. 3,873,607) | 6 | ethyl 9-oxo-16-hydroxy-16-vinyl-3-oxa-13-trans-prostenoate |
| 91 | 2-(6-carbethoxy-5-oxahexyl)-2-cyclopentenone (U.S. Pat. No. 3,873,607) | 11 | ethyl 9-oxo-16-hydroxy-16-cyclopropyl-3-oxa-13-trans-prostenoate |

EXAMPLES 92-99

Saponification of the 16-substituted-16-hydroxy prostenoic acid alkyl esters of Table 10 below with 0.5N potassium hydroxide in 10:1 methanol water at room temperature for 24 hours followed by acidification and ether extraction provides the 16-substituted-16-hydroxy prostadienoic or prostenoic acids of the Table.

TABLE 10

| Example | Starting Prostadienoic or Prostenoic acid alkyl esters of Example | Product Prostadienoic or Prostenoic acid |
|---|---|---|
| 92 | 84 | 9-oxo-16-hydroxy-16-cyclopropyl-5-cis-13-trans-prostadienoic acid |
| 93 | 85 | 9-oxo-16-hydroxy-16-vinyl-5-cis,13-trans-prostadienoic acid |
| 94 | 86 | 9-oxo-16-hydroxy-16-cyclopropyl-13-trans-prostenoic acid |
| 95 | 87 | 9-oxo-16-hydroxy-16-vinyl-13-trans-prostadienoic acid |
| 96 | 88 | 9-oxo-16-hydroxy-16-vinyl-3-thia-13-trans-prostenoic acid |
| 97 | 89 | 9-oxo-16-hydroxy-16-cyclopropyl-3-thia-13-trans-prostenoic acid |
| 98 | 90 | 9-oxo-16-hydroxy-16-vinyl-3-oxa-13-trans-prostenoic acid |
| 99 | 91 | 9-oxo-16-hydroxy-16-cyclopropyl-3-oxa-13-trans-prostenoic acid |

EXAMPLE 100

Preparation and separation of
9α,11α,16-trihydroxy-16-cyclopropyl-5-cis-13-trans-prostadienoic acid and
9β,11α,16-trihydroxy-16-cyclopropyl-5-cis-13-trans-prostadienoic acid To a stirred, ice-cold solution of 360 mg of 9-oxo-11α,16-dihydroxy-16-cyclopropyl-5-cis,13-trans-prostadienoic acid (Example 33) in 50 ml of ethanol is added 408 mg of sodium borohydride in small portions during 1 minute. The mixture is stirred at 0° for 5 minutes and at ambient temperature for 1.5 hours. The bulk of the ethanol is evaporated at room temperature, and the residue is partitioned with cold dilute hydrochloric acid and ethyl acetate. The organic phase is separated and washed with water and brine, dried over magnesium sulfate and concentrated. The residue is subjected to chromatography on silica gel to give (first eluted) an oil, 9β,11α,16-trihydroxy-16-cyclopropyl-5-cis,13-trans-prostadienoic acid, pmr (acetone-$d_6$): δ 3.6 (multiplet, 16-$\underline{H}$) and 3.95 (multiplet, 9α-$\underline{H}$ and 11β-$\underline{H}$) and (second eluted) and oil, 9α, 11α,16-trihydroxy-16-cyclopropyl-5-cis,13-trans-prostadienoic acid, pmr spectum (acetone-$d_6$): δ 3.90 (multiplet, 11β-$\underline{H}$) and 4.10 (multiplet, 9β-$\underline{H}$).

EXAMPLE 101-119

Treatment of the 9-oxo-prostaglandins of Table 11 below with sodium borohydride by the procedure of Example 100 followed by chromatography is productive of the 9α-hydroxy and 9β-hydroxy prostaglandins of the table.

TABLE 11

| Example | Starting 9-oxo-prostadienoic or prostenoic acid of Example | Product 9α/β,11α,16-trihydroxy-prostadienoic or prostenoic acid |
|---|---|---|
| 101 | 34 | 9α/β,11α,16-trihydroxy-16-cyclopropyl-20-nor-13-trans-pros- |

TABLE 11-continued

| Example | Starting 9-oxo-prostadienoic or prostenoic acid of Example | Product 9α/β,11α,16-trihydroxy-prostadienoic or prostenoic acid |
|---|---|---|
| 102 | 35 | tenoic acid<br>9α/β,11α,16-trihydroxy-16-cyclopropyl-20-methyl-13-trans-prostenoic acid |
| 103 | 36 | 9α/β,11α,16-trihydroxy-16-cyclopropyl-20-ethyl-13-trans-prostenoic acid |
| 104 | 37 | 9α/β,11α,16-trihydroxy-16-vinyl-20-nor-13-trans-prostenoic acid |
| 105 | 38 | 9α/β,11α,16-trihydroxy-16-vinyl-20-methyl-13-trans-prostenoic acid |
| 106 | 39 | 9α/β,11α,16-trihydroxy-16-vinyl-20-ethyl-13-trans-prostenoic acid |
| 107 | 40 | 9α/β,11α,16-trihydroxy-16-cyclopropyl-13-trans-prostenoic acid |
| 108 | 41 | 9α/β,11α,16-trihydroxy-16-cyclopropyl-20-nor-5-cis,13-trans-prostadienoic acid |
| 109 | 42 | 9α/β,11α,16-trihydroxy-16-cyclopropyl-20-methyl-5-cis,13-trans-prostadienoic acid |
| 110 | 43 | 9α/β,11α,16-trihydroxy-16-cyclopropyl-20-ethyl-5-cis,13-trans-prostadienoic acid |
| 111 | 44 | 9α/β,11α,16-trihydroxy-16-vinyl-20-nor-5-cis,13-trans-prostadienoic acid |
| 112 | 45 | 9α/β,11α,16-trihydroxy-16-vinyl-20-methyl-5-cis,13-trans-prostadienoic acid |
| 113 | 46 | 9α/β,11α,16-trihydroxy-16-vinyl-20-ethyl-5-cis,13-trans-prostadienoic acid |
| 114 | 47 | 9α/β,11α,16-trihydroxy-16-vinyl-5-cis,13-trans-prostadienoic acid |
| 115 | 7 | 9α/β,11α,16-trihydroxy-16-vinyl-13-trans-prostenoic acid. |
| 116 | 48 | l-9α/β,11α,16-trihydroxy-16-vinyl-13-trans-prostenoic acid methyl ester |
| 117 | 49 | l-9α/β,11α,16-trihydroxy-16-cyclopropyl-5-cis-13-trans-prostadienoic acid methyl ester |
| 117a | 49A | 9α/β,11α,16-trihydroxy-16-vinyl-5-cis-13-trans-2a,2b-bishomo-prostadienoic acid. |
| 117b | 49B | 9α/β,11α,16-trihydroxy-16-cyclopropyl-5-cis,13-trans-2a,2b-bishomoprostadienoic acid. |
| 118 | 92 | 9α/β,16-dihydroxy-16-cyclopropyl-5-cis-13-trans-prostadienoic acid |
| 119 | 93 | 9α/β,16-dihydroxy-16-vinyl-5-cis-13-trans-prostadienoic acid |
| 119A | 97 | 9α/β,16-dihydroxy-16-cyclopropyl-13-trans-3-thiaprostenoic acid |
| 119B | 98 | 9α/β,16-dihydroxy-16-vinyl-13-trans-3-oxaprostenoic acid |

EXAMPLES 120-125

Treatment of the prostadienoic or prostenoic acids listed in Table 12 below with the indicated diazoalkane in the following manner provides the product prostadienoate or prostenoate esters of the Table.

An ethereal solution containing a molar excess of diazoalkane is added to a solution of the carboxylic acid in ether or ether-acetone. After 10 to 30 minutes the solution is carefully evaporated and the residual ester is purified in the usual way by chromatography on silica gel.

TABLE 12

| Example | Diazoalkane | Starting Prostadienoic or Prostenoic Acid of Example | Product Prostadienote or Prostenoate Ester |
|---|---|---|---|
| 120 | diazomethane | 33 | methyl 9-oxo-11α,16-dihydroxy-16-cyclopropyl-5-cis,13-trans-Prostadienoate |
| 121 | diazoethane | 47 | ethyl 9-oxo-11α,16-dihydroxy-16-vinyl-5-cis,13-trans-pros- |

TABLE 12-continued

| Example | Diazoalkane | Starting Prostadienoic or Prostenoic Acid of Example | Product Prostadienote or Prostenoate Ester |
|---|---|---|---|
| 122 | 1-diazo-butane | 40 | n-butyl 9-oxo-11α,16-dihydroxy-16-cyclopropyl-13-trans-prostenoate |
| 123 | 1-diazo-decane | 7 | n-decyl 9-oxo-11α,16-dihydroxy-16-vinyl-13-trans-prostenoate |
| 124 | 1-diazo-hexane | 36 | hexyl 9-oxo-11α,16-dihydroxy-16-cyclopropyl-20-ethyl-13-trans-prostenoate |
| 125 | 1-diazo-octane | 39 | octyl 9-oxo-11α,16-dihydroxy-16-vinyl-20-ethyl-13-trans-prostenoate |

EXAMPLES 126–129

Treatment of the carboxy-cyclopentenones or carbomethoxy-cyclopentenones of Table 13 with chlorotrimethylsilane by the procedure described in U.S. Pat. No. 3,873,607 (Example 958) is productive of the bis-trimethylsilylether esters or trimethylsilylether methyl esters of the Table.

TABLE 13

| Example | Starting Cyclopentenone | Product ether |
|---|---|---|
| 126 | 2-(6-carboxyhexyl)-4-hydroxy-cyclopent-2-en-1-one[1] | 4-trimethylsiloxy-2-(6-carbotrimethylsiloxyhexyl)-cyclopent-2-en-1-one |
| 127 | l-2-(6-carbomethoxyhexyl)-4-hydroxycyclopent-2-en-1-one[2] | l-4-trimethylsiloxy-2-(6-carbomethoxy)-cyclopent-2-en-1-one |
| 128 | l-2-(6-carbomethoxy-2-cis-hexenyl)-4-hydroxycyclopent-2-en-1-one[3] | l-4-trimethylsi oxy-2-(6-carbomethoxy-2-cis-hexenyl)cyclopent-2-en-1-one |
| 129 | 2-(6-carboxy-2-cisoctenyl)-4-hydroxycyclopent-2-en-1-one[4] | 2-(6-carbotrimethysiloxy-2-cis-octenyl)-4-trimethylsiloxy-cyclopent-2-en-1-one |
| 129A | 2-(6-carboxy-5-oxahexyl)-4-hydroxycyclopent-2-en-1-one[4] | 4-trimethylsiloxy-2-(6-carbotrimethsiloxy-5-oxahexyl)-cyclopent-2-en-1-one |

References:
[1]U.S. Pat. No. 3,873,607.
[2]Pappo et al., Tetrahedron Letters, 943 (1973).
[3]Bruhn et al., Ibid., 235 (1976)
[4]U.S. Pat. No. 3,950,406.

EXAMPLES 130–131

Treatment of the 11α-hydroxyprostaglandins of Table 14 by the procedure of Pike et al., Journ. of Org. Chem., 84 3552, 1974 is productive of the $\Delta^{8,12}$prostaglandins of the Table.

TABLE 14

| Example | Starting 11α-hydroxy prostaglandin | Product $\Delta^{8,12}$ prostaglandins |
|---|---|---|
| 130 | 33 | 9-oxo-16-hydroxy-16-vinyl-$\Delta^{8,12}$ 5-cis,13-trans-prostatrienoic acid |
| 131 | 37 | 9-oxo-16-hydroxy-16-cyclopropyl $\Delta^{8,12}$,13-trans-prostadienoic acid. |

EXAMPLE 132

Preparation of
11-oxo-9α,16-dihydroxy-16-cyclopropyl-5-cis,13-trans-prostadienoic acid To a stirred solution of 135 mg. of 9α,11α,16-trihydroxy-16-cyclopropyl-5-cis,13-trans-prostadienoic acid (Example 50) in 25 ml. of acetone and 3 ml of acetic acid at −40° C. is added 0.15 ml. (0.4 mmoles) of Jones Reagent. After 2 hours at −40° C. to −35° C. a few drops of isopropanol are added, and the resulting mixture is partitioned with water and ether. The ether extract is washed with water and brine, dried over magnesium sulfate, and concentrated with the oil of toluene. The residue is purified by column chromatography on silica gel with hexane progressively enriched in ethyl acetate to provide an oil, pmr spectrum (acetone-d$_6$): δ 2.71 (quartet, 10-H's) and 4.44 (triplet, 9-H).

EXAMPLES 133–151

The 11-oxo-9α,16-dihydroxy-prostadienoic or prostenoic acids of Table 15 below are prepared by oxidation of the precursor 9α,11α,16-trihydroxy-precursors with Jones Reagent by the procedure of Example 132.

TABLE 15

| Example | Starting 9α,11α,16-trihydroxy-prostadienoic or prostenoic acid of Example | Product 11-oxo-9α,16-dihydroxy-prostadienoic or prostenoic acid |
|---|---|---|
| 133 | 51 | 11-oxo-9α,16-dihydroxy-16-cyclopropyl-20-nor-13-trans-prostenoic acid |
| 134 | 52 | 11-oxo-9α,16-dihydroxy-16-cyclopropyl-20-methyl-13-trans-prostenoic acid |

TABLE 15-continued

| Example | Starting 9α,11α,16 prostadienoic or prostenoic acid of Example | Product 11-oxo-9α,16-dihydroxy-prostadienoic or prostenoic acid |
|---|---|---|
| 135 | 53 | 11-oxo-9α,16-dihydroxy-16-cyclopropyl-20-ethyl-13-trans-prostenoic acid |
| 136 | 54 | 11-oxo-9α,16-dihydroxy-16-vinyl-20-nor-13-trans-prostenoic acid |
| 137 | 55 | 11-oxo-9α,16-dihydroxy-16-vinyl-20-methyl-13-trans-prostenoic acid |
| 138 | 56 | 11-oxo-9α,16-dihydroxy-16-vinyl-20-ethyl-13-trans-prostenoic acid |
| 139 | 57 | 11-oxo-9α,16-dihydroxy-16-cyclopropyl-13-trans-prostenoic acid |

Starting 9α,11α,16 prostadienoic or prostenoic acid of Example

| Example | | Product 11-oxo-9α,16-dihydroxy-prostadienoic or prostenoic acid |
|---|---|---|
| 140 | 58 | 11-oxo-9α,16-dihydroxy-16-cyclopropyl-20-nor-5-cis,13-trans-prostadienoic acid |
| 141 | 59 | 11-oxo-9α,16-dihydroxy-16-cyclopropyl-20-methyl-5-cis,13-trans-prostadienoic acid |
| 142 | 60 | 11-oxo-9α,16-dihydroxy-16-cyclopropyl-20-ethyl-5-cis,13-trans-prostadienoic acid |
| 143 | 61 | 11-oxo-9α,16-dihydroxy-16-vinyl-20-nor-5-cis,13-trans-prostadienoic acid |
| 144 | 62 | 11-oxo-9α,16-dihydroxy-16-vinyl-20-methyl-5-cis,13-trans-prostadienoic acid |
| 145 | 63 | 11-oxo-9α,16-dihydroxy-16-vinyl-20-ethyl-5-cis,13-trans-prostadienoic acid |
| 146 | 64 | 11-oxo-9α,16-dihydroxy-16-vinyl-5-cis,13-trans-prostadienoic acid |

Starting 9α,11α,16-trihydroxy-prostadienoic or prostenoic acid of Example

TABLE 15-continued

| Example | | Product 11-oxo-9α,16-dihydroxy-prostadienoic or prostenoic acid |
|---|---|---|
| 147 | 65 | 11-oxo-9α,16-dihydroxy-16-vinyl-13-trans-prostenoic acid |
| 148 | 66 | l-11-oxo-9α,16-dihydroxy-16-vinyl-13-trans-prostenoic acid |
| 149 | 67 | l-11-oxo-9α,16-dihydroxy-16-cyclopropyl-5-cis-13-trans-prostadienoic acid methyl ester |
| 150 | 67A | 11-oxo-9α,16-dihydroxy-16-vinyl-5-cis,13-trans-2a,2b-bishomo-prostadienoic acid |
| 151 | 67B | 11-oxo-9α,16-dihydroxy-16-cyclopropyl-5-cis,13-trans-2a,2b-bis-homoprostadienoic acid |
| 152 | 67C | 11-oxo-9α,16-dihydroxy-16-cyclopropyl-13-trans-prostenoic acid |
| 153 | 67D | 11-oxo-9α,16-dihydroxy-16-vinyl-13-trans-prostenoic acid |

The compounds of this invention are useful as bronchodilators for the treatment of asthma and chronic bronchitis. Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung*, 18, 955 (1968).]

In Table 16 which follows bronchodilator activity for representative compounds of this invention against one or more of three spasmogenic agents is expressed as an $ED_{50}$ determined from the results obtained with three logarithmic cummulative intravenous doses. In this assay, these compounds of this invention provide an effect of longer duration than does natural 1-PGE$_1$ or 1-PGE$_2$.

TABLE 16

Bronchodilator Activity (Konzett Assays)

| | $ED_{50}$, mg./kg. Spasmogenic Agent | | |
|---|---|---|---|
| COMPOUND | 5-hydroxytryptamine | histamine | Acetylcholine |
| 9-oxo-11α,16-dihydroxy-16-vinyl-13-trans-prostenoic acid | 0.00186 | 0.00111 | 0.760 |

We claim:
1. A compound of the formula:

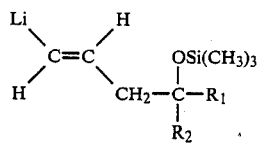

wherein $R_1$ is an alkyl or alkenylmethyl group having 3 to 7 carbon atoms or said alkyl or alkenylmethyl group is substituted with one or two alkyl groups having one to three carbon atoms and wherein $R_2$ is a substituent selected from the group consisting of vinyl and cyclopropyl.

2. The compound according to claim 1 wherein $R_2$ is vinyl.

3. The compound according to claim 1 wherein $R_1$ is an alkyl group of four carbon atoms.

4. The compound according to claim 3 wherein $R_2$ is vinyl.

5. A compound of the formula:

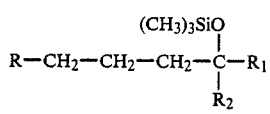

wherein

R is a moiety selected from the group consisting of MgBr and

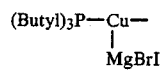

$R_1$ is an alkyl or alkenylmethyl group of 3 to 7 carbon atoms or said alkyl or alkenylmethyl group substituted with one or two alkyl groups of one to three carbon atoms, and wherein $R_2$ is vinyl or cyclopropyl.

6. The compound according to claim 5 wherein $R_2$ is vinyl and $R_1$ is an alkyl group having four carbon atoms.

7. A compound of the formula:

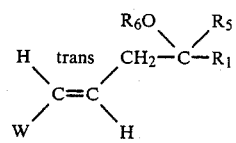

wherein W is iodine or tri-n-butylstannyl, $R_5$ is vinyl or cyclopropyl, $R_6$ is hydrogen or triloweralkylsilyl and $R_1$ is an alkyl or alkenylmethyl group having 3 to 7 carbon atoms, or said alkyl or alkenylmethyl group substituted with one or two alkyl groups of one to three carbon atoms.

8. The compound according to claim 7 wherein $R_5$ is vinyl.

9. The compound according to claim 7 wherein W is iodine.

10. The compound according to claim 7 wherein W is tri-n-butylstannyl.

11. The compound according to claim 9 wherein $R_5$ is vinyl.

12. The compound according to claim 10 wherein $R_5$ is vinyl.

13. The compound according to claim 11 wherein $R_1$ is an alkyl group of four carbon atoms.

14. The compound according to claim 12 wherein $R_1$ is an alkyl group of four carbon atoms.

* * * * *